US012727913B2

(12) United States Patent
Wang

(10) Patent No.: US 12,727,913 B2
(45) Date of Patent: Sep. 8, 2026

(54) CANNULA ADAPTER AND SURGICAL ROBOT

(71) Applicant: CORNERSTONE TECHNOLOGY (SHENZHEN) LIMITED, Shenzhen (CN)

(72) Inventor: Zerui Wang, Shenzhen (CN)

(73) Assignee: CORNERSTONE TECHNOLOGY (SHENZHEN) LIMITED, Shenzhen (CN)

( * ) Notice: Subject to any disclaimer, the term of this patent is extended or adjusted under 35 U.S.C. 154(b) by 175 days.

(21) Appl. No.: 18/620,653

(22) Filed: Mar. 28, 2024

(65) Prior Publication Data

US 2024/0238010 A1 Jul. 18, 2024

Related U.S. Application Data

(63) Continuation of application No. PCT/CN2022/116377, filed on Aug. 31, 2022.

(30) Foreign Application Priority Data

Sep. 30, 2021 (CN) .......................... 202111161668.0

(51) Int. Cl.
*A61B 17/34* (2006.01)
*A61B 17/00* (2006.01)
*A61B 34/30* (2016.01)

(52) U.S. Cl.
CPC .......... *A61B 17/3423* (2013.01); *A61B 34/30* (2016.02); *A61B 2017/00367* (2013.01); (Continued)

(58) Field of Classification Search
CPC ................ A61B 17/3423; A61B 34/30; A61B 2034/302; A61B 2017/00367; A61B 2017/00486
See application file for complete search history.

(56) References Cited

U.S. PATENT DOCUMENTS 8,182,469 B2 * 5/2012 Anderson .............. A61B 90/57 606/1
9,060,795 B2 * 6/2015 Meenink ................ A61B 34/74
(Continued)

FOREIGN PATENT DOCUMENTS

CN 102398266 A 4/2012
CN 102398266 B * 3/2014 ............ B25J 15/028
(Continued)

OTHER PUBLICATIONS

Cornerstone Technology (Shenzhen) Limited, Extended European Search Report, EP 22874538.6, Nov. 19, 2024, 12 pgs.
(Continued)

*Primary Examiner* — Terrell L Mckinnon
*Assistant Examiner* — Ding Y Tan
(74) *Attorney, Agent, or Firm* — ScienBiziP, P.C.

(57) ABSTRACT

The present disclosure discloses a cannula adapter and a surgical robot. The cannula adapter includes an adapter body, a first guide member, a clamping jaw, an operating actuation mechanism, and a follower mechanism. The first guide member is fixedly disposed in the adapter body. The clamping jaw is disposed in the adapter body and limited by the first guide member, and is configured to translate between a first position and a second position in a guiding direction of the first guide member. The follower mechanism is configured to be driven by the operating actuation mechanism to move. The follower mechanism and at least one clamping jaw are cooperatively movable, the at least one clamping jaw is in the first position when the follower mechanism is in a third position, and the at least one clamping jaw is in the second position when the follower mechanism is in a fourth position.

20 Claims, 10 Drawing Sheets

(52) U.S. Cl.
CPC ............... *A61B 2017/00486* (2013.01); *A61B 2034/302* (2016.02)

(56) References Cited

U.S. PATENT DOCUMENTS

| | | | | |
|---|---|---|---|---|
| 10,456,208 | B2 * | 10/2019 | Thompson | A61B 17/3476 |
| 2012/0068484 | A1 * | 3/2012 | Xu | B25J 15/028 294/103.1 |
| 2015/0374445 | A1 | 12/2015 | Gombert et al. | |
| 2017/0086930 | A1 | 3/2017 | Thompson et al. | |
| 2018/0168689 | A1 * | 6/2018 | Beckman | A61B 17/3498 |
| 2019/0053824 | A1 * | 2/2019 | Scheib | A61B 34/70 |
| 2019/0125405 | A1 * | 5/2019 | Beckman | A61B 90/50 |
| 2020/0107896 | A1 | 4/2020 | Thompson et al. | |

FOREIGN PATENT DOCUMENTS

| | | | | | |
|---|---|---|---|---|---|
| CN | 209404947 | U | * | 9/2019 | |
| CN | 111281497 | A | | 6/2020 | |
| CN | 112494142 | A | | 3/2021 | |
| CN | 213320219 | U | | 6/2021 | |
| CN | 113349934 | | | 9/2021 | |
| CN | 113442116 | A | | 9/2021 | |
| CN | 113598957 | A | | 11/2021 | |
| CN | 216455279 | U | | 5/2022 | |
| CN | 216495630 | U | | 5/2022 | |
| CN | 216702633 | U | | 6/2022 | |
| CN | 112494142 | B | * | 9/2025 | A61B 34/70 |
| DE | 10122311 | A1 | * | 12/2001 | A61B 90/11 |
| WO | WO-2015142814 | A1 | * | 9/2015 | A61B 34/30 |

OTHER PUBLICATIONS

Cornerstone Technology (Shenzhen) Limited, International Search Report with English translation, PCT/CN2022/116377, Nov. 18, 2022, 7 pgs.

* cited by examiner

160

CANNULA ADAPTER AND SURGICAL ROBOT

CROSS REFERENCE TO RELATED APPLICATIONS

The present disclosure is a continuation of PCT Patent Application No. PCT/CN2022/116377, filed Aug. 31, 2022, which claims priority to Chinese Patent application Ser. No. 202111161668.0, entitled "CANNULA ADAPTER AND SURGICAL ROBOT," filed Sep. 30, 2021, each of which is incorporated by reference herein in its entirety.

TECHNICAL FIELD

The present disclosure relates to the technical field of medical devices, and more specifically to a cannula adapter and a surgical robot.

BACKGROUND

A minimally invasive surgical robot with a master-slave configuration can assist a surgeon in achieving precise positioning during surgery. This type of robot has a benefit of reducing the patient's wound, resulting in a shorter post-operative recovery time. Additionally, the robot provides a stable operating platform that can compensate for the tremor of the surgeon, so it is widely used in clinical surgeries.

A surgical robot at a patient side performs surgical operations using a surgical instrument having an end effector. Conventional surgical instruments include scissors, clamps, etc. In general, wire ropes are employed to manipulate the end effector to pitch, yaw and grip.

At a human body side, an opening is made on a patient's abdomen using an instrument called a cannula to create a passage for access to an abdominal cavity. A marking point of the cannula is aligned with the opening of the patient's abdomen at first. Then, the surgical instrument is inserted through a channel of the cannula into the patient's body, and the cannula supports an elongated tube of the surgical instrument due to its rigidity to avoid deformation of the elongated tube. In the early stage after the opening is made on the abdomen, gas is filled in the abdominal cavity through a hole of the cannula, allowing expansion of the abdominal cavity to make space for operations of the surgical instrument. Cannulas have various types and lengths depending on various types of surgical instruments and various thicknesses of patients' abdominal cavities in the surgery, such as a type for an instrument with a diameter of 8 mm, a type for an instrument with a diameter of 5 mm, and a type for a camera, etc. It can be seen that cannulas play a crucial role in surgical robots.

Correspondingly, a structure of the robot to which the cannula is connected is called a cannula adapter. The cannula adapter is required to be easily and quickly engaged with the cannula under manual operations and securely connected to the cannula without wobbling.

Due to a large range of motion of a robotic arm and the fact that three to four robotic arms are involved in the surgery at the same time, a size of the cannula adapter needs to be as small as possible in order to prevent interference to or compression on a human body or interference between the robotic arms.

At the beginning of setup of a surgery, the body and cannula are relatively fixed and immovable once the cannula is inserted into the body. At this time, a control button on the robotic arm of the surgical robot can be pressed to allow the robotic arm to move when being dragged, allowing the robotic arm to be dragged towards the cannula for engaging. Typically, medical staff use one hand to drag the robotic arm and the other hand to hold the cannula. Therefore, efficient operation and cooperation among the cannula, robotic arm, and cannula adapter are crucial to the period and convenience of the surgical preparation procedure.

SUMMARY

A series of concepts in a simplified form are introduced in the Summary of the present disclosure, which will be described in further detail in the detailed description. The Summary of the present disclosure is not intended to limit key features and essential technical features of the claimed technical solutions, and is not intended to determine the protection scope of the claimed technical solutions.

Embodiments of the first aspect of the present application provide a cannula adapter, and the cannula adapter includes: an adapter body; a first guide member fixedly disposed in the adapter body; at least one clamping jaw disposed in the adapter body and limited by the first guide member, where the at least one clamping jaw configured to translate between a first position and a second position in a guiding direction of the first guide member; an operating actuation mechanism; and a follower mechanism configured to be driven by the operating actuation mechanism to move; where the follower mechanism and the at least one clamping jaw are cooperatively movable, the at least one clamping jaw is in the first position when the follower mechanism is in a third position, and the at least one clamping jaw is in the second position when the follower mechanism is in a fourth position.

In the cannula adapter provided in the first aspect of the present disclosure, the clamping jaw is designed to move in a translational manner, which improves the reliability of the clamping, and this kind of arrangement also enables the direction of the clamping force to coincide with the center line of the claw tip, which can reduce the deviation error during clamping.

Embodiments of a second aspect of the present disclosure further provide a cannula adapter, and the cannula adapter includes: an adapter body; a second guide member, where the second guide member is fixedly connected to the adapter body; a movable member, where the movable member is limited by the second guide member and movable in a guiding direction of the second guide member, and the movable member has at least one biasing part, and where each of the at least one biasing part has a first limitation surface; a first guide member, where the first guide member is fixedly connected to the adapter body, a projection of an extension direction of the first guide member and a projection of an extension direction of the second guide member on a same plane intersect each other and have an intersection angle in a range of 85° to 90°; at least one clamping jaw configured to clamp a cannula, where the at least one clamping jaw is limited by the first guide member and movable in a guiding direction of the first guide member, each of the at least one clamping jaw has a biasing mate matching with a respective biasing part of the at least one biasing part, and the first limitation surface limits a position of the biasing mate; an elastic assembly disposed in the adapter body and configured to provide a driving force to cause the at least one clamping jaw to move along the guiding direction of the first guide member to be in a clamping state; and a handle, where the handle includes: a hinge part, where the handle is hinged to the adapter body via the hinge part, an operating part disposed outside the adapter body and fixedly connected to the hinge part, and an execution part disposed in the adapter body and fixedly connected to the hinge part, where the execution part is movably connected to the movable part; where the handle is configured to pull the movable member to move along the guiding direction of the second guide member via the execution part so as to enable the at least one clamping jaw to move along the guiding direction of the first guide member through interaction between the respective biasing part and the biasing mate.

According to the cannula adapter provided in the second aspect of the present disclosure, the operator can complete clamping and releasing of a pair of clamping jaws by using the handle with one hand, which enables the operator to use the other hand to complete other actions such as operating the matched cannula, so that the operation is more convenient. The design of the clamping jaw moving along a guide rail greatly simplifies the structure, making the movement of the clamping jaws smaller, saving space, and easier to realize self-locking, thereby improving reliability of the clamping. This kind of arrangement also make the direction of the clamping force coincide with the center line of the claw tip, so that the deviation error during clamping is reduced.

In an embodiment, a projection of an extension direction of the first guide member and a projection of the second guide member on a same plane have an intersection angle in a range of 89° to 90° so as to enable the at least one clamping jaw to translate along the first guide member; and the elastic assembly is connected between the adapter body and the movable member and configured to provide a driving force to cause the movable member to move along the guiding direction of the second guide member, so as to enable the at least one clamping jaw to move along the guiding direction of the first guide member to be in the clamping state through the interaction between the respective biasing part and the biasing mate.

In an embodiment, each of the at least one clamping jaw includes a clamping part and a connecting part connected to each other, where the connecting part is movably connected to the first guide member, and the biasing part is disposed at the connecting part.

In an embodiment, the clamping part of each of the at least one clamping jaw has an end portion provided with a claw tip facing the cannula, the claw tip has an included angle in a range of 80° to 100°, and a center line of the included angle of the claw tip and a direction of a clamping force of a respective clamping claw of the at least one clamping claw are in a same straight line.

In an embodiment, the connecting part defines a through hole, the first guide member has a cross-sectional shape adapted to the through hole, and the first guide member extends into the through hole.

In an embodiment, the at least one clamping jaw is in the clamping state when the biasing mate is at a first end of the first limitation surface, and the clamping jaw is in an open state when the biasing mate is at a second end of the first limitation surface; and where a slope of a plane tangent to the first limitation surface at the second end relative to the second guide member is greater than a slope of a plane tangent to the first limitation surface at the first end relative to the second guide member.

In an embodiment, at least a part of the first limitation surface extends from the first end to the second end, and a slope of a plane tangent to the part of the first limitation surface relative to the second guide member increases gradually.

In an embodiment, the slope of the plane tangent to the part of the first limitation surface at the first end relative to the second guide member is smallest.

In an embodiment, the slope of the plane tangent to the first limitation surface at the first end is less than or equal to 0.3.

In an embodiment, the respective biasing part further has a second limitation surface, and a space for accommodating the biasing mate is defined by the second limitation surface and the first limitation surface; and where a variation trend of a slope of a plane tangent to the second limitation surface is the same as a variation trend of the slope of the plane tangent to the first limitation surface.

In an embodiment, the biasing mate is configured as a sliding member or a rolling member.

In an embodiment, the handle is at an initial position when the at least one clamping jaw is in the clamping state, the handle is at a working position when the at least one clamping jaw is in an open state, and the execution part has an initial position and a working position that are located on a same side of the hinge part in a vertical direction.

In an embodiment, the execution part has a moment arm approaching zero when the at least one clamping jaw and a cannula have a largest distance.

In an embodiment, the operating part and the execution part are at least partially odd-symmetric or centrosymmetric with respect to the hinge part, and an extension direction of the operating part and an extension direction of the execution part are both tangent to the hinge part.

In an embodiment, the adapter body has an upper surface provided with an avoidance part, and the operating part is inserted into the avoidance part when the operating part is in a working position.

Embodiments of a third aspect of the present disclosure provide a surgical robot, including the cannula adapter according to the first aspect or the second aspect.

According to the surgical robot provided in the third aspect of the present application, a technical effect similar to the cannula adapter in the first aspect or the second aspect can be achieved.

BRIEF DESCRIPTION OF THE DRAWINGS

The following drawings of the present disclosure are used herein as part of the present disclosure for understanding the present disclosure. The embodiments of the present disclosure and the description thereof are shown in the drawings to explain the principles of the present disclosure.

DETAILED DESCRIPTION OF THE EMBODIMENTS

Figure 1:
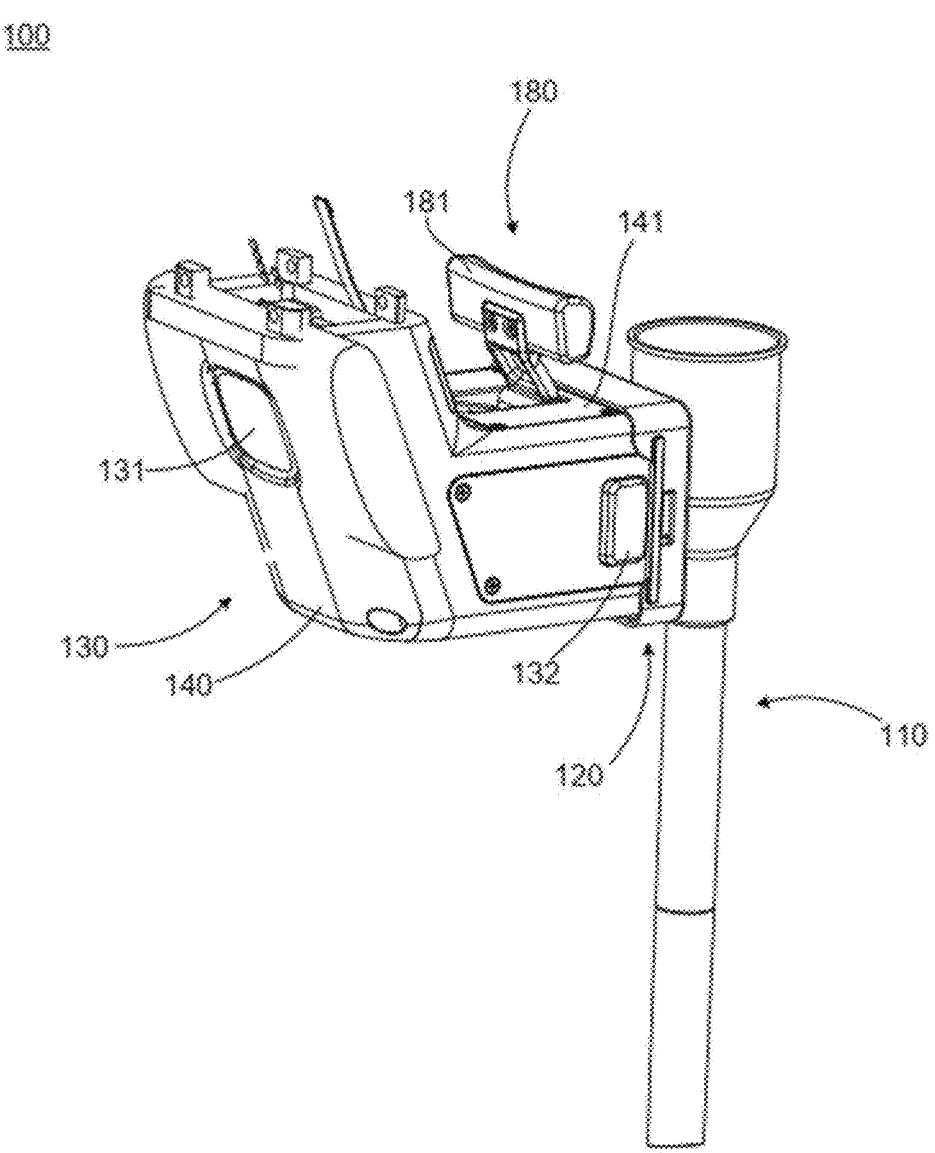
FIG. 1 is a perspective view of a partial structure of a surgical robot according to an optional embodiment of the present disclosure.
Figure 2:
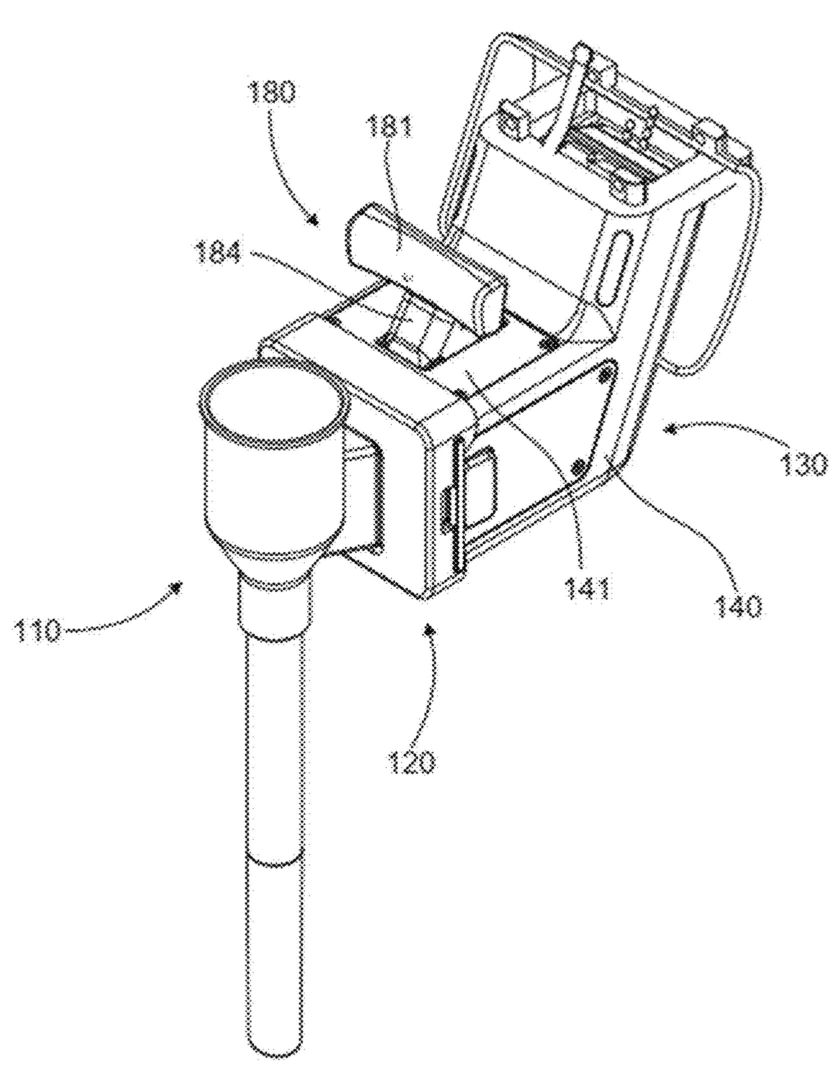
FIG. 2 is another perspective view of a partial structure of the surgical robot in FIG. 1.
Figure 3:
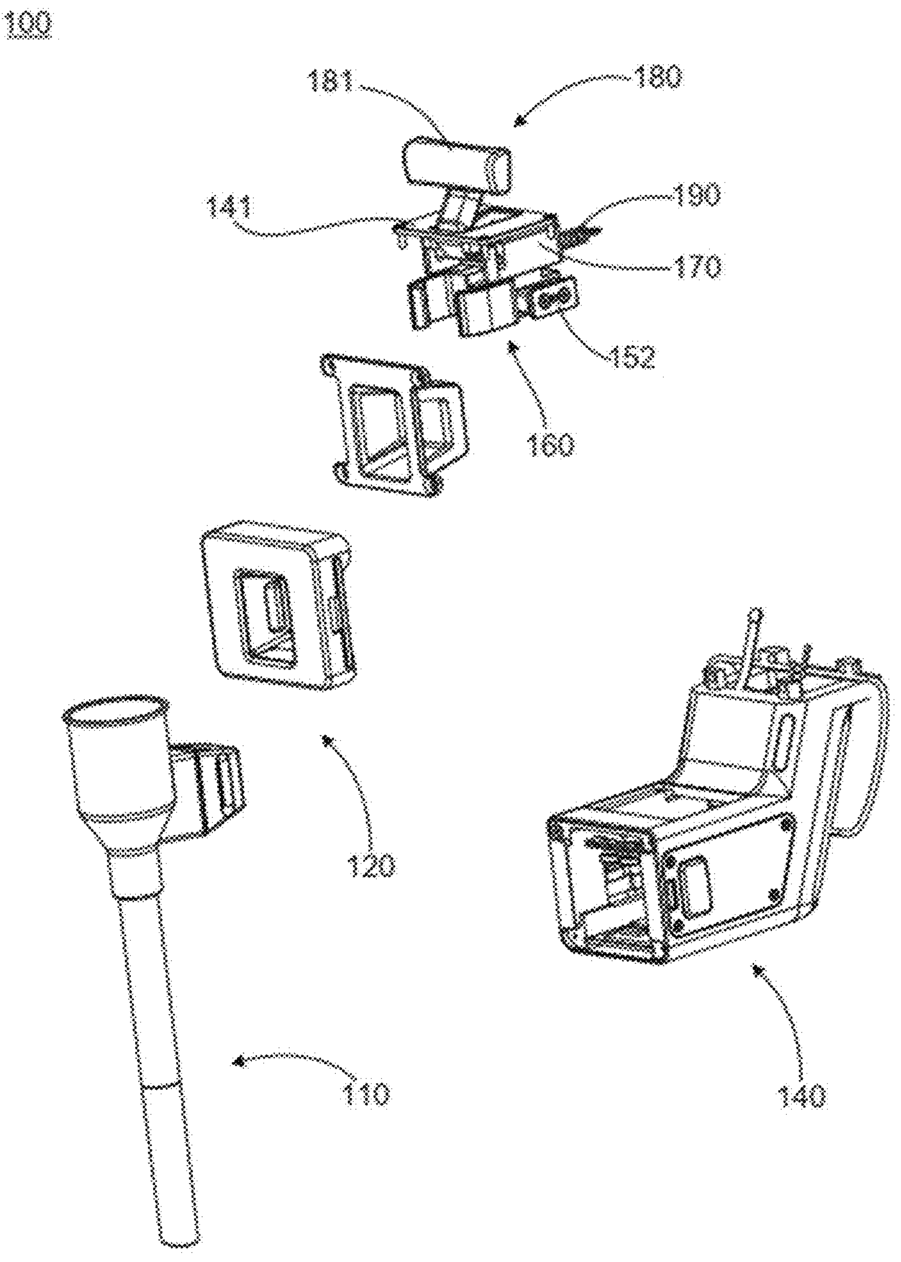
FIG. 3 is an exploded view of a partial structure of the surgical robot in FIG. 1.
Figure 4:
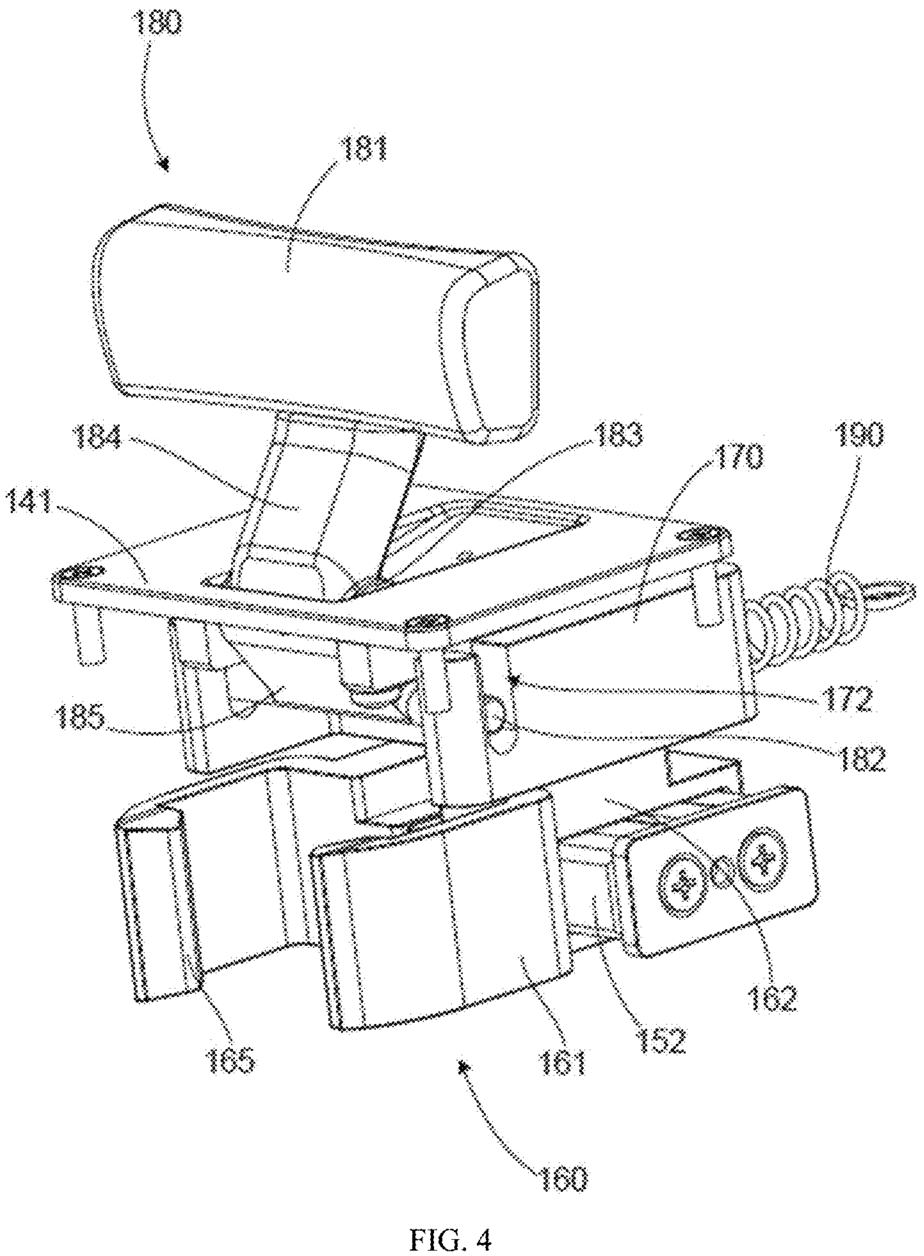
FIG. 4 is a partial schematic structural diagram of a cannula adapter according to an optional embodiment of the present disclosure.
Figure 5:
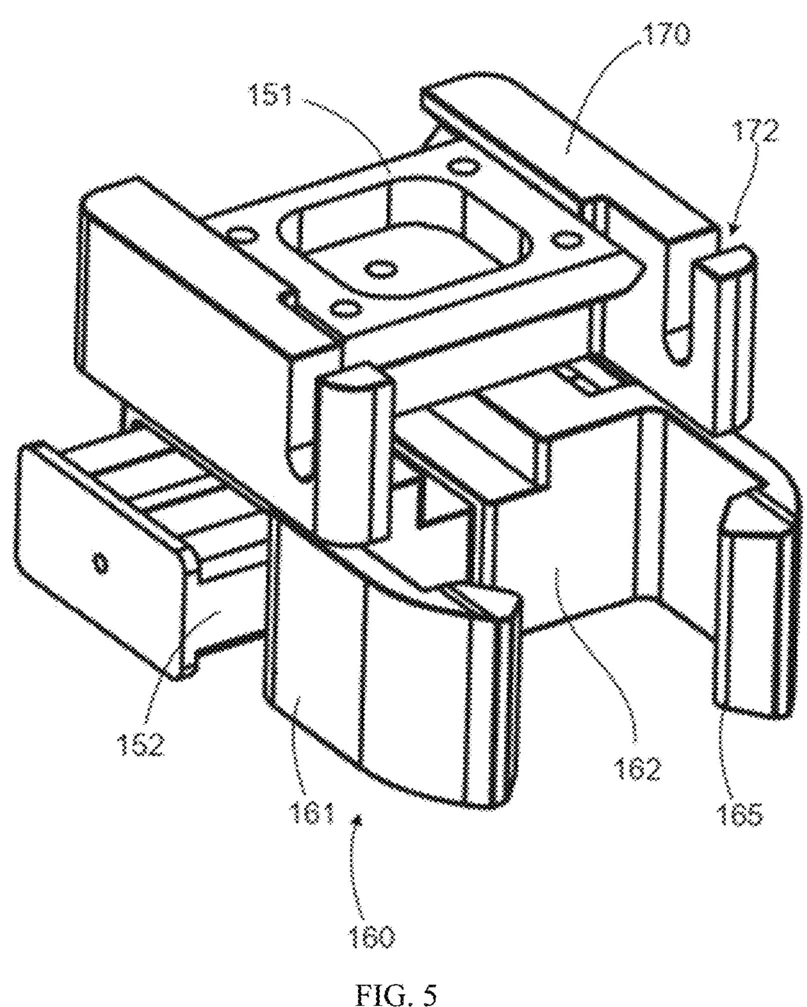
FIG. 5 is a schematic diagram of FIG. 4 in which an upper panel and a handle are removed.
Figure 6:
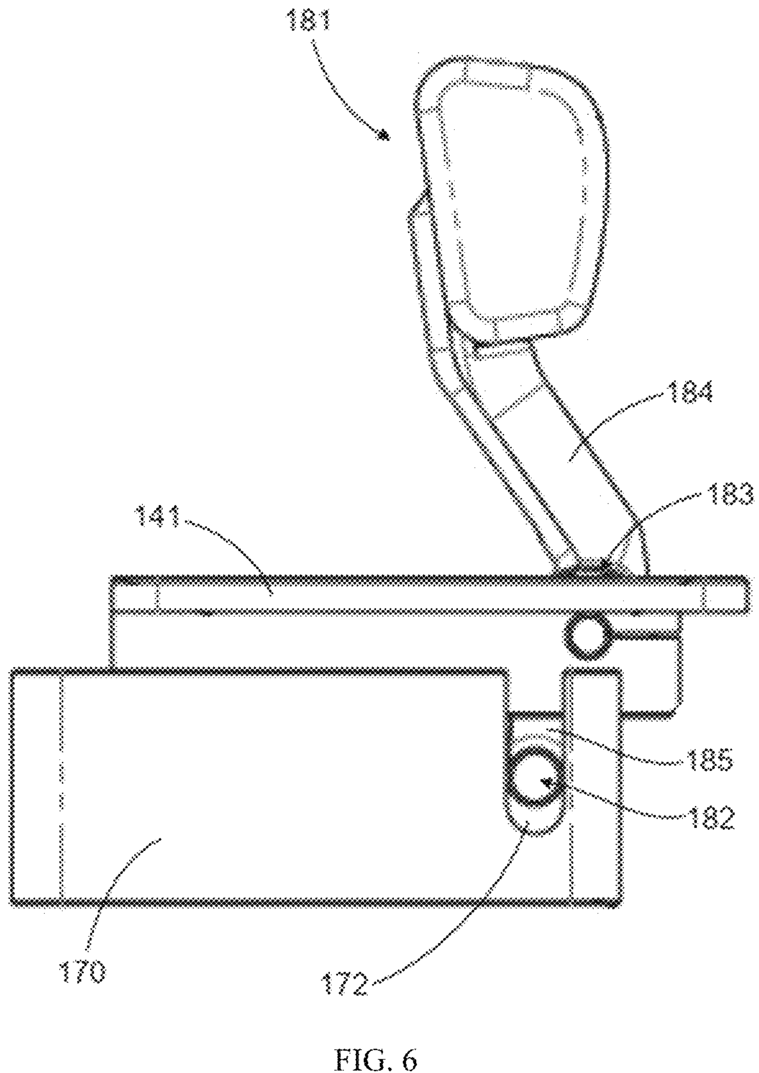
FIG. 6 is a schematic side view of an installation state of a handle and a movable member of a cannula adapter according to an optional embodiment of the present disclosure.

In the following description, a number of specific details are given in order to provide a more thorough understanding of the present disclosure. However, it is apparent to those skilled in the art that embodiments of the present disclosure are able to be implemented without one or more of these details. In other examples, some technical features that are well known in the art are not described in order to avoid confusion with the embodiments of the present disclosure.

For a thorough understanding of the present disclosure, detailed descriptions are provided in the following description. It should be understood that these embodiments are provided to make the disclosure of the present disclosure thorough and complete, and fully convey the concepts of the exemplary embodiments to those of ordinary skill in the art. Obviously, implementation of the embodiments of the present disclosure is not limited to special details familiar to those skilled in the art. The preferred embodiments of the present disclosure are described in detail below, but in addition to these detailed descriptions, the present disclosure may further have other implementations.

It should be noted that the terminology used herein is for the purpose of describing particular embodiments only and is not intended to be limiting of exemplary embodiments in accordance with the present disclosure. As used herein, singular forms are also intended to include plural forms as well, unless the context clearly indicates otherwise. Furthermore, it should be further understood that the terms 'includes,' 'including,' 'comprises,' and/or 'comprising,' when used herein, specify the presence of stated features, integers, steps, operations, elements, and/or components, but do not exclude the presence or addition of one or more other features, integers, steps, operations, elements, components, and/or groups thereof.

Ordinal terms such as 'first' and 'second' cited in the present disclosure are merely identifiers and do not have any other meanings, such as a particular order, etc. Moreover, for example, the term 'first part' does not by itself imply the existence of a 'second part', and the term 'second part' does not by itself imply the existence of a 'first part'. The terms 'top,' 'bottom,' 'front,' 'rear,' 'left,' 'right,' 'inside,' 'outside,' and similar expressions are used in the present disclosure for the purpose of illustration and not limitation.

The inventor finds that conventional cannula adapters have many problems such as large occupied space, difficult one-handed operation, poor convenience, complex structure and the like. In addition, clamping jaws in the conventional cannula adapters for clamping the cannula are mostly configured to pivot, and deviation between a direction of a clamping force and a clamping position easily occurs during pivoting of the clamping jaw, resulting in unstable clamping and the like.

Now, exemplary embodiments according to the present disclosure will be described in more detail with reference to FIG. 1 to FIG. 12.

First, referring to FIG. 1 to FIG. 5, a surgical robot 100 in the present disclosure has one or more robotic arms. The robotic arm includes a cannula 110, a cannula adapter 130, and a sterile adapter 120. The sterile adapter 120 is first mounted to and locked to the cannula adapter 130, both of which may be separated by a sterile dressing or the like. Then, the cannula 110 is mounted to the sterile adapter 120 to enable the cannula 110 to be locked by the cannula adapter 130.

The cannula adapter 130 includes an adapter body 140, and the adapter body 140 may be a housing of the cannula adapter 130. An interactive lamp (not shown), an unlock button 132, a drag control button 131, and the like may be disposed on the adapter body 140. For ease of illustration, an end portion of the cannula adapter 130 close to the cannula 110 is defined as a front portion, and an end portion of the cannula adapter 130 away from the cannula 110 and opposite to the front portion is defined as a rear portion.

The drag control button 131 is provided at the rear portion of the cannula adapter 130, which may act as a movement control component of the robot arm. For example, when the drag control button 131 is in a normal state (not being pressed), the robotic arm is in a locked state, i.e., the robotic arm cannot be moved. After an operator presses the drag control button 131, the robotic arm is unlocked, which is able to be dragged and moved by the operator.

The unlock button 132 is provided at a position near the front portion of the cannula adapter 130, which may act as a connection control component between the sterile adapter 120 and the cannula adapter 130. For example, the sterile adapter 120 and the cannula adapter 130 are connected by a snap, a hook, or other manners, and the unlock button 132 is configured to unlock this connection. That is, the sterile adapter 120 can be removed from the sterile adapter 130 after the operator presses the unlock button 132.

The interactive lamp may display various types of light signals according to various sensors disposed in the adapter body 140 to indicate a current state of the cannula adapter 130. The interactive lamp may be provided at any position for easy observation, which, in this embodiment, is provided at a position near the unlock button 132.

The cannula adapter 130 further includes an operating actuation mechanism, clamping jaws 160, a first guide member, a follower mechanism, and a second guide member.

The clamping jaws 160 are disposed in the adapter body 140 and each clamping jaw 160 has a connecting part 162 and a clamping part 161, an end portion of the clamping part 161 is provided with a claw tip 165 for clamping the cannula 110. In the process of clamping the cannula with the clamping jaws 160, the clamping jaws 160 move in a translation manner. In a natural state, the clamping jaws 160 are in a clamping position, which is called a first position in this embodiment. When manually actuated, the clamping jaws 160 are moved to a non-clamping position, which is called a second position in this embodiment.

A mechanism for manually actuating the clamping jaws 160 is the operating actuation mechanism, which may be a pulling handle or a pressing handle having a connecting part configured to drag the follower mechanism. In this embodiment, a structure of the handle 180 is given as an example.

The follower mechanism is a connecting member that can be actuated by the operating actuation mechanism. In an implementation, the follower mechanism may be a cam mechanism or a linkage mechanism having a part that can be controlled by the operating actuation mechanism and a part that is cooperatively moveable with the clamping jaws. During the cooperative movement of the follower mechanism and the clamping jaws, the clamping jaws are in the first position when the follower mechanism moves to a third position, and the clamping jaws are in the second position when the follower mechanism moves to a fourth position. In an embodiment, a specific structure of the movable member 170 is given as an example of the follower mechanism.

A cooperatively moveable structure of the follower mechanism and the clamping jaws includes a track surface on the follower mechanism, and a passive mechanism mounted to the clamping claws, such as a roller or a bearing which can move back and forth on the track surface. When the follower mechanism is controlled by the operating actuation mechanism to move in the first direction, the movement of the follower mechanism in the first direction is converted into a translational movement of the clamping jaws in the second direction due to limitation of the track surface.

Specifically, referring to FIG. 4 to FIG. 6 and FIG. 7 to FIG. 12, the second guide member 151 is fixedly connected to the adapter body 140. Optionally, the adapter body 140 has a detachable upper panel 141, and the second guide member 151 may be fixedly connected to an inner surface of the upper panel 141, for example, may be fixedly connected to the inner surface of the upper panel 141 by screws.

In an embodiment, the follower mechanism is configured as a movable member 170. The movable member 170 is disposed below the second guide member 151, and is engaged to shoulders of the second guide member 151, so as to be movable along the second guide member 151. Alternatively, two ends of the second guide member 151 are tapered outwards, and the movable member 170 has grooves correspondingly fitted with the tapered ends, i.e., the movable member 170 below the second guide member 151 is engaged to the tapered ends of the second guide member 151. Optionally, the movable member 170 is symmetric with respect to the second guide member 151. The movable member 170 has a biasing part 171.

Referring to FIG. 3 to FIG. 5 and FIG. 7 to FIG. 12, the clamping jaws 160 and the first guide member 152 are disposed in the adapter body 140, and an extension direction of the first guide member 152 is not parallel to an extension direction of the second guide member 151. Optionally, projections of the first guide member 152 and the second guide member 151 on the same plane (or horizontal plane) intersect each other, and an intersection angle of the projections is in a range of 85° to 90°. Optionally, the intersection angle of the projections of the first guide member 152 and the second guide member 151 on the same plane (or horizontal plane) is in a range of 89° to 90°.

In this embodiment, the first guide member 152 may be disposed along a width direction of the cannula adapter 130, or may be disposed laterally. That is, the first guide member 152 is disposed perpendicular to the second guide member 151. Optionally, the first guide member 152 is connected between two inner walls of the adapter body 140 opposite to each other.

In an alternative embodiment, the first guide member 152 is further configured as a substantially symmetrical V-shaped structure with a tip disposed toward the cannula 110, so as to cause the clamping jaws 160 to tilt forwardly close to the cannula 110 as it moves along the first guide member 152. In this case, the projections of the first guide member 152 and the second guide member 151 on the horizontal plane intersect at a vertex of the V-shaped structure, an intersection angle of the projections is in range of 170° to 180°, and an included angle between each wing portion of the V-shaped structure and the second guide member 151 is in a range of 85° to 90°.

In another alternative embodiment, the first guide member 152 is also configured as a substantially symmetrical V-shaped structure with a tip facing away from the cannula 110. In this case, the clamping jaws 160 are able to substantially tilt backwardly close to the cannula 110 during closing, so as to create a backward (i.e., a direction pointed by the tip of the V-shaped structure) pulling force on the cannula 110 when clamping the cannula 110. That is, the clamping jaws 160 not only create a force in a direction of clamping the cannula 110, but also create a partial force that enables the cannula 110 to be inserted towards the rear of the cannula adapter, which further improves the clamping stability. An included angle of the V-shaped structure is also in a range of 170° to 180°.

In the illustrated embodiment, the first guide member 152 is configured as a '-' shaped structure, that is, an extension direction of the first guide member 152 is perpendicular to an extension direction of the second guide member 151.

The connecting part 162 is connected to the first guide member 152, so that the clamping jaws 160 can move along the guiding direction of the first guide member 152.

Each clamping jaw 160 has a biasing mate 163. The biasing part 171 and the biasing mate 163 cooperate with each other to operate. The biasing part 171 has a track surface, so that the biasing mate can move along the track surface. The track surface has both a component in a translation direction of a respective clamping jaw and a component in a moving direction of a movable member. For example, when the movable member 170 moves on the second guide member 151, the biasing part 171 squeezes the biasing mate 163 to cause the clamping jaws 160 to move along the guiding direction of the first guide member 152. Thus, a distance between the pair of clamping jaws 160 changes to cause the pair of clamping jaws 160 to clamp the cannula 110 or release the cannula 110, and the biasing mate 163 on each clamping jaw 160 may be disposed at any position on the connecting part 162. As a result, a movement manner of the clamping jaws 160 is changed from pivoted clamping to translational clamping in this embodiment, which enables the clamping force to be located exactly on a center line of the claw tip 165, i.e., the clamping force overlaps with the middle line of the claw tip 165, and avoids deviation error between a direction of the clamping force and a clamping position due to deflection generated by pivoting of the clamping jaws 160 during the pivoted clamping.

Figure 12:
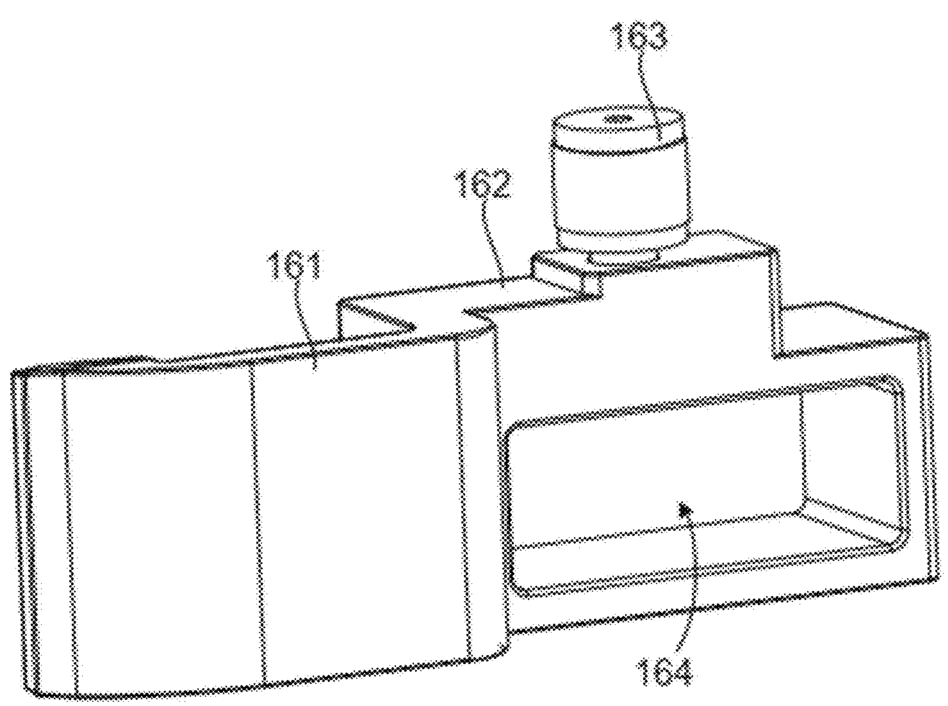
FIG. 12 is a perspective view of the clamping jaw in FIG. 7.

Specifically, the connecting part 162 defines a through hole 164 (as shown in FIG. 12), and a shape of the through hole 164 is adapted to a cross-sectional shape of the first guide member 152, so that the connecting part 162 of each clamping jaw 160 can be sleeved on the first guide member 152. In this embodiment, the cross-sectional shape of the first guide member 152 and the shape of the through hole 164 are square. It is easy to understand that the cross-sectional shape of the first guide member 152 and the shape of the through hole 164 may also be circular, elliptical, or other shapes.

In an alternative embodiment, the cannula adapter 130 has only one clamping jaw 160, and the cannula 110 is clamped between the clamping jaw 160 and an inner wall of the adapter body 140.

In another alternative embodiment, one clamping jaw 160 and one clamping plate (not shown) may be provided, and the clamping part 161 of the clamping jaw 160 faces the clamping plate. The clamping plate has a clamping part, the connecting part 162 and the biasing mate 163, and an end portion of the clamping part does not have a claw tip. The clamping plate extends beyond the adapter body 140 to the sterile adapter 120 or the cannula 110, and is disposed on a side of the sterile adapter 120 or the cannula 110 to create a lifting and squeezing effect on the side of the sterile adapter 120 or the cannula 110 to facilitate the clamping operation.

Optionally, in order to obtain a better clamping effect, the cannula adapter 130 includes a pair of clamping jaws 160. Claw tips 165 of respective clamping parts 161 of the pair of clamping jaws 160 are bent towards each other (or bent inwards) to achieve inward clamping of the pair of clamping jaws 160. Optionally, the pair of clamping jaws 160 may also be symmetrical with respect to the second guide member 151.

In this embodiment, when the pair of clamping jaws 160 clamp the cannula 110, a distance between the pair of clamping jaws 160 is the smallest.

Optionally, a center line of an included angle of a claw tip 165 and a clamping force of a clamping jaw 160 are in the same straight line. Optionally, the center line of the included angle of the claw tip 165 is perpendicular to the clamping part 161 and/or the connecting part 162. The included angle of the claw tip 165 is in a range of 80° to 100°. Optionally, the included angle of the claw tip 165 is 90°. Due to the above setting of the claw tip 165, the clamping jaw 160 is more easily fitted with the cannula 110. Thus, the proper setting of the angle of the claw tip 165 allows the cannula 110 to be separated from the mechanism by force when the mechanism is accidentally stuck. In addition, the included angle of about 90° of the claw tip 165 not only avoids an excessively small guiding adaptation range during the clamping process of the clamping jaw 160, but also avoids an excessively sharp included angle that would result in an enclosing curtain-type sterile adapter 120 being embedded in the cannula 110 and unable to be detached from the cannula 110.

As described above, the clamping jaw 160 clamps through translational movement, which allows for less movement of the clamping jaw 160 during clamping, so that a mounting space in the cannula adapter 130 is larger. In addition, a non-pivoting clamping manner or translational clamping manner is more responsive to the driving force. In particular, the driving force has a greater component in the clamping direction in the case of this embodiment, resulting in less effort on the operation of the user.

As shown in FIG. 4, FIG. 7, FIG. 8, and FIG. 10, an elastic assembly 190 is disposed in the adapter body 140 and acts on the pair of clamping jaws 160 to provide a driving force to enable the pair of clamping jaws 160 to move inwards along the first guide 152 toward each other, i.e., clamping parts 161 of the pair of clamping jaws 160 inwardly clamp.

In this embodiment, the elastic assembly 190 is optionally configured as a spring. The elastic assembly 190 is disposed between the adapter body 140 and the movable member 170 along a length direction of the clamping jaw 160, i.e., is disposed longitudinally. Specifically, one end of the elastic assembly 190 is connected to the adapter body 140, and the other end of the elastic assembly 190 is connected to the movable member 170, so that the spring is longitudinally disposed in a larger space, which is beneficial to generating greater elastic force.

Optionally, the elastic assembly 190 may also be connected between a pair of claiming jaws 160, i.e., laterally disposed (not shown). Specifically, the elastic assembly 190 may be laterally disposed at any position on the clamping part 161, and optionally, may be disposed at a position on the clamping part 161 close to the connecting part 162. As a result, the operator can operate the handle 180 with less effort. It is easy to understand that the elastic assembly 190 may also be connected between the connecting parts 162 of the pair of clamping jaws 160.

Structures of the movable member 170 and the biasing parts 171 are described in detail below with reference to FIG. 7 to FIG. 12. Each biasing part 171 has a first limitation surface 176. As an example, the first limitation surface 176 may be configured as a side surface of the movable member 170 facing the biasing mate 163. The biasing part 171 has a first end 174 and a second end 175. When the distance between the clamping jaw 160 and the cannula 110 is the smallest, or when the distance between the pair of clamping jaws 160 is the smallest, the clamping jaws 160 clamp the cannula 110, i.e., the clamping jaws 160 are considered to be in the clamping state, and at this time, the biasing mate 163 is at the first end 174.

When the distance between the clamping jaw 160 and the cannula 110 is the largest, or when the pair of clamping jaws 160 are separated from the cannula 110 and are separated from each other by a maximum degree, it is considered that the clamping jaws 160 are in an open state, and at this time, the biasing mate 163 is at the second end 175. In other words, the first end 174 corresponds to the clamping state of the clamping jaws 160, and the second end 175 corresponds to the opening state of the clamping jaws 160. The biasing mate 163 is movable between the first end 174 and the second end 175 of the biasing part 171 when the clamping jaws 160 are switched between the clamping state and the open state. The biasing mate 163 may be configured as a sliding member or a rolling member. In order to reduce friction, the biasing mate 163 may optionally be configured as the rolling member, which may be, for example, a bearing.

As an implementation, the first end 174 corresponds to the clamping state and is close to the cannula 110, the second end 175 corresponds to the open state and is away from the cannula 110. It is easy to understand that the second end 175 corresponding to the clamping state and the first end 174 corresponding to the open state can also be realized by changing a direction of movement of the handle 180 (described in detail below) and/or a driving direction of the elastic force.

For ease of understanding, the term 'slope' used below, for example, 'a slope of a plane tangent to the first limitation surface 176 relative to the second guide member 151 at the first end 174' refers to 'a slope of a line formed by intersection of the first limitation surface 176 and a horizontal plane relative to a longitudinal straight line on the horizontal plane at the first end 174', and so on.

A slope of a plane tangent to the first limitation surface 176 relative to the second guide 151 at the first end 174 is greater than a slope of a plane tangent to the first limitation surface 176 relative to the second guide member 151 at the second end 175. In other words, a slope of the line formed by the intersection of the first limitation surface 176 and the horizontal plane relative to the longitudinal straight line on the horizontal plane at the first end 174 is less than a slope of the line formed by the intersection of the first limitation surface 176 and the horizontal plane relative to the longitudinal straight line on the horizontal plane at the second end 175. It is easy to understood that the slope of the first limitation surface 176 at the first end 174 is less than the slope at the second end 175.

When the cannula adapter 130 in which the biasing part 171 has a small slope at the first end 174 and a larger slope at the second end 175 in the present disclosure is in use, a smaller movement of the movable member 170 is required to cause a larger movement of the clamping jaws 160 along the first guide member 152, which enables the operator to break the handle 180 with a smaller range of motion of the hand, making one-handed operation more friendly. Meanwhile, a smaller elastic force is required to drive the clamping jaws 160 to move and prevent the clamping jaws 160 from moving away from each other, thereby facilitating the clamping of the clamping jaws 160. In addition, the design of the small slope of the biasing part 171 at the first end 174 is also beneficial to adaptation of cannulas of different specifications, i.e., has high adaptability.

Optionally, the first limitation surface 176 has a part extending from the first end 174 to the second end 175, and a slope of a plane tangent to the part of the first limitation surface 176 relative to the second guide member 151 gradually increases. In other words, the slope of the line formed by the intersection of the first limitation surface 176 and the horizontal plane relative to the longitudinal straight line on the horizontal plane gradually increases from the first end 174 to the second end 175. That is, the slope of the first limitation surface 176 becomes larger and larger from the first end 174 to the second end 175. Therefore, the gradual slope design can, on the one hand, enable the pair of clamping jaws 160 to be further away from each other by moving a smaller distance, and on the other hand, make the cooperation of the first limitation surface 176 of the movable member 170 and the biasing mate 163 smoother, so that the motion of the biasing mate 163 does not have any sense of jumping, and the operator has a better feeling during use.

When the biasing part 171 is provided with only the first limitation surface 176, only one of the elastic force of the spring and the driving force of the operator can act on the clamping jaws 160 or the movable member 170. As an example, when the elastic assembly 190 is connected between the movable member 170 and the adapter body 140 and provides a tensile force, the driving force of the operator may cause the pair of clamping jaws 160 to open or move away from each other, while the tensile force cannot cause the clamping jaws 160 to close. In this case, the elastic assembly 190 needs to be provided between the pair of clamping jaws 160 to provide the elastic force that causes the clamping jaws 160 to clamp.

Figure 7:
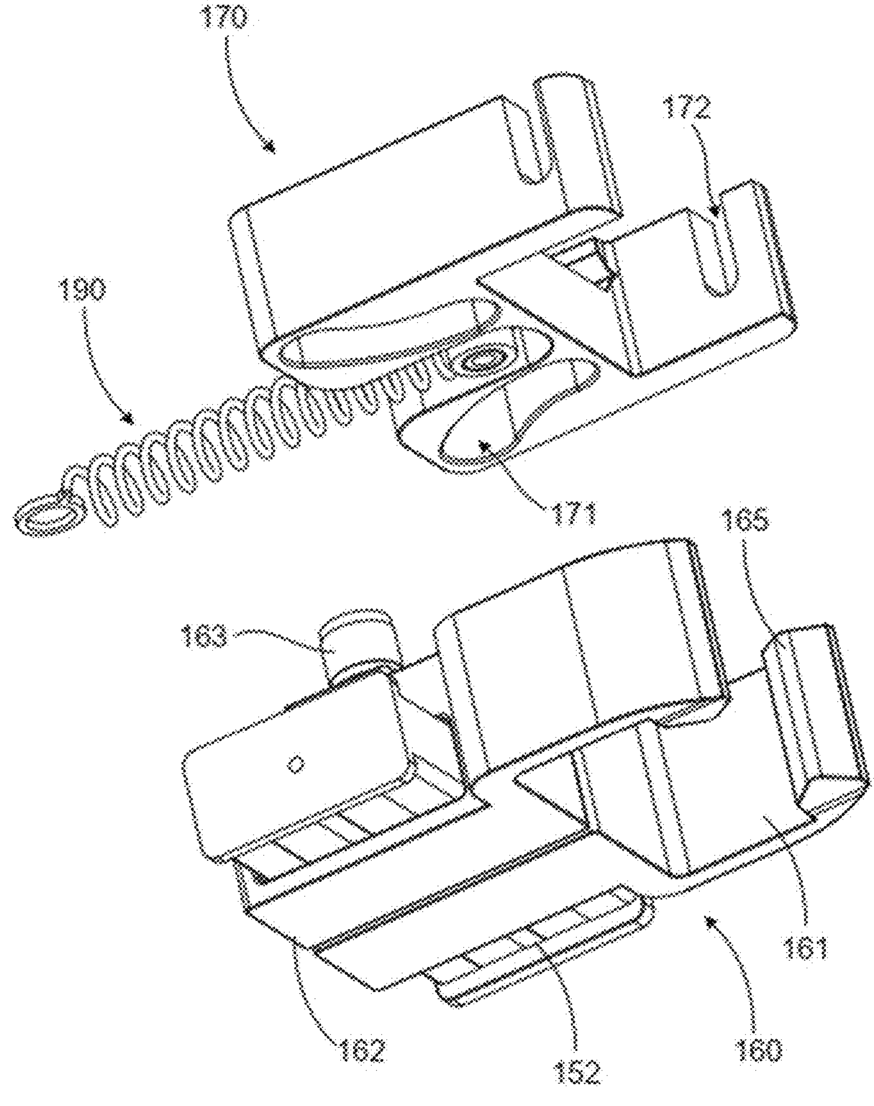
FIG. 7 is a schematic diagram of a partial structure in FIG. 4 in a separation state.
Figure 8:
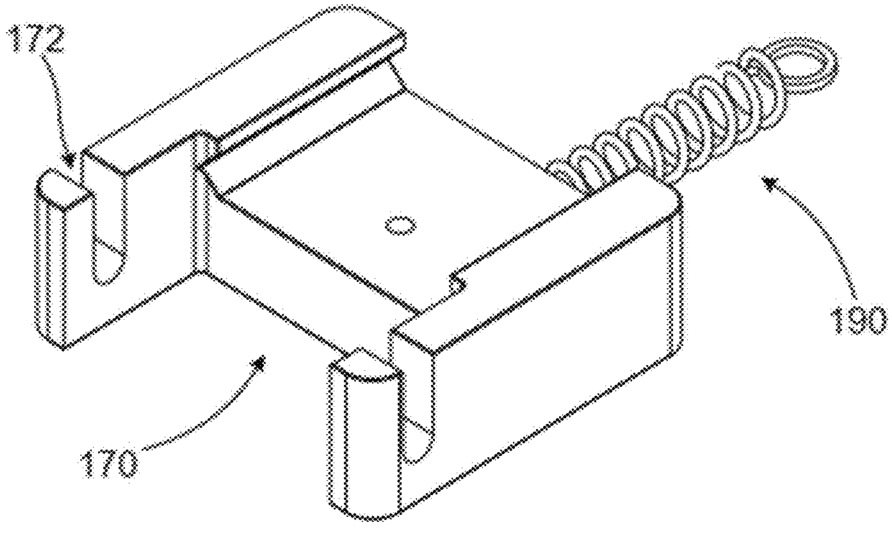
FIG. 8 is a schematic diagram of a movable member in FIG. 7 from another view.
Figure 9:
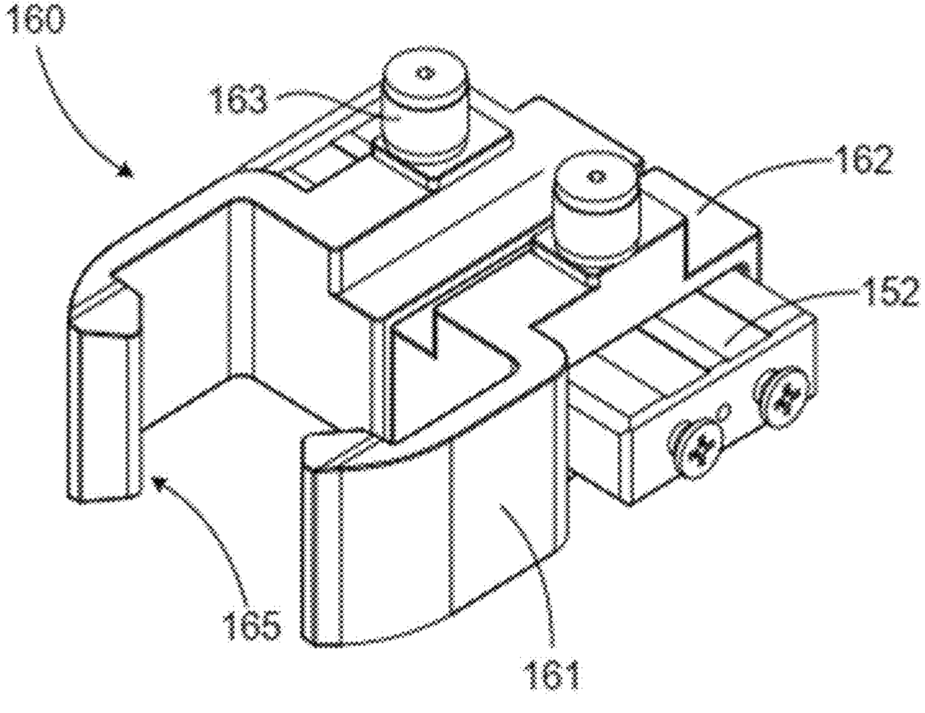
FIG. 9 is a schematic diagram of a clamping jaw and a first guide member in FIG. 7 from another view.
Figure 10:
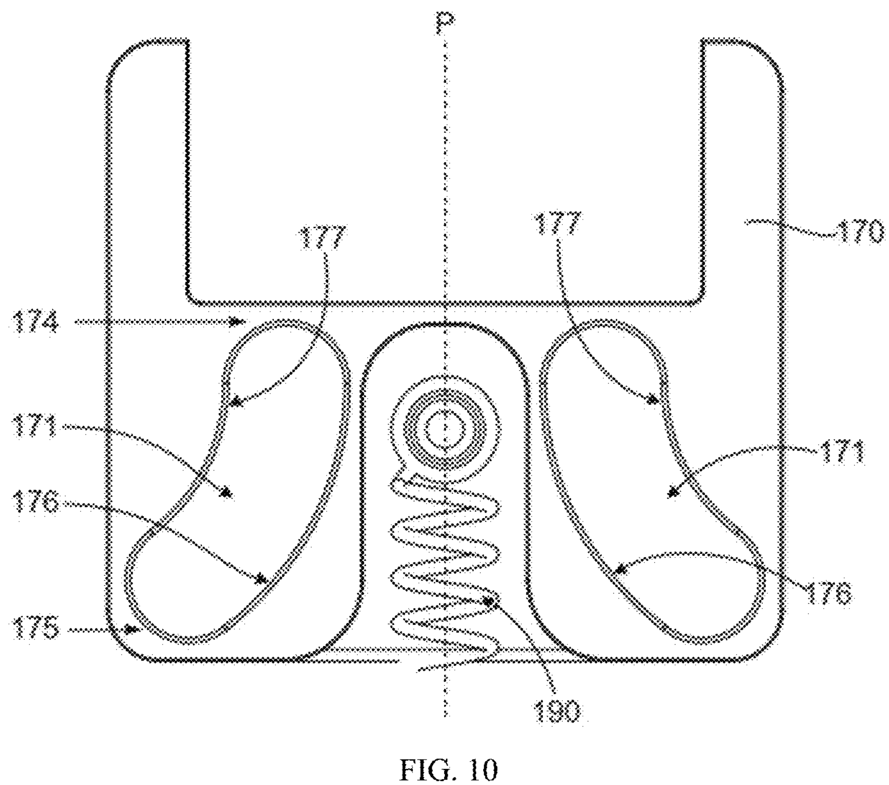
FIG. 10 is a bottom view of the movable member in FIG. 7.
Figure 11:
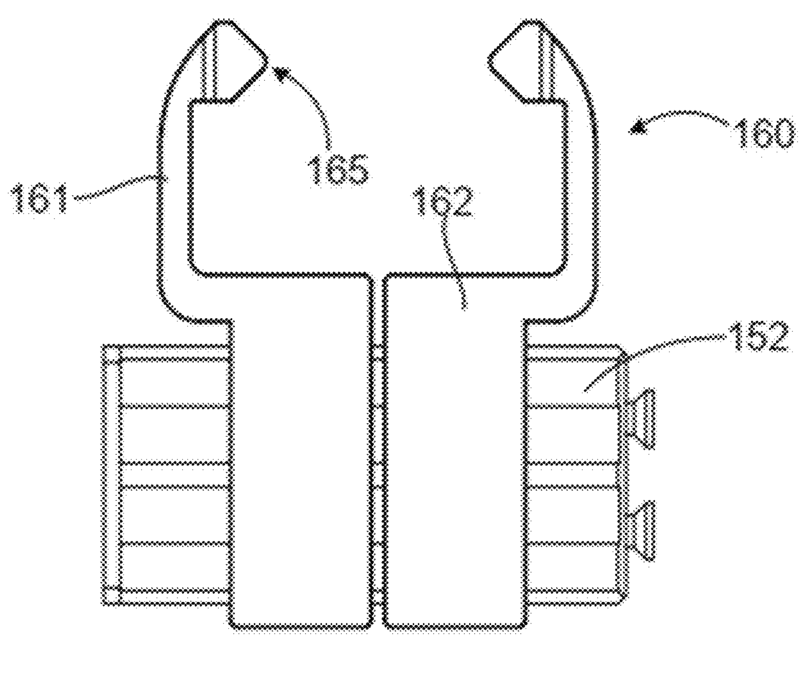
FIG. 11 is a bottom view of the clamping jaw and the first guide member in FIG. 7.

In the embodiment shown in FIG. 7, the biasing part 171 further has a second limitation surface 177, and a space for accommodating the movement of the biasing mate 163 is defined by the second limitation surface 177 and the first limitation surface 176. Optionally, the biasing part 171 is configured to a waist-shaped groove penetrating the movable member 170, and further has a second limitation surface 177 spaced apart from the first limitation surface 176 and extending from the first end 174 to the second end 175. In other words, the first limitation surface 176 and the second limitation surface 177 are configured as two cylindrical surfaces of inner walls of the waist-shaped groove. It is easy to understand that a variation trend of a slope of the second limitation surface 177 is the same as a variation trend of the slope of the first limitation surface 176, that is, the slope of the line formed by the intersection of the second limitation surface 177 and the horizontal plane relative to the longitudinal straight line on the horizontal plane gradually increases from the first end 174 to the second end 175. In other words, the first limitation surface 176 may be parallel to the second limitation surface 177. The second limitation surface 177 is designed, so that the biasing mate 163 can follow the trajectory of the second limitation surface 177 when resetting from the open state to the clamping state of the clamping jaws 160, thereby reducing the vibration caused by the large elastic force and prolonging the service life.

Thus, the two limitation surfaces interfere with the biasing mate 163 in both movement directions of the biasing mate 163. Specifically, when the elastic assembly 190 is disposed between the adapter body 140 and the movable member 170 and provides the tensile force as described above, i.e., when the elastic assembly 190 is a tension spring, the movable member 170 tends to move in a direction away from the cannula 110, and the second limitation surface 177 can push the biasing mate 163 to cause the pair of clamping jaws 160 to be close to each other or to be clamped. On the contrary, when the operator overcomes the elastic force to drive the movable member 170 to move in a direction close to the cannula 110, the first limitation surface 176 interferes with the biasing mate 163 to cause the clamping jaws 160 to be away from each other or to be open. The arrangement of the elastic assembly 190 being connected between the adapter body 140 and the movable member 170 as described above, i.e., dual limitations of the first limitation surface 176 and the second limitation surface 177, is beneficial to saving space and vacates space for the installation of other components, so that the integration of the overall system is higher, and the function of the overall system is more complete.

In addition, such a variable slope design, compared to the design of a constant small slope, reduces a length of movement of the movable member 170 and a relative stretching length of the spring, and also enables the pair of clamping jaws 160 to be further away from each other. In addition to the tension spring, the elastic assembly 190 may also be in the form of other springs such as a compression spring, and only the pulling direction of the handle 180 needs to be adjusted adaptively.

The first limitation surface 176 and the second limitation surface 177 in this embodiment are configured as smooth curved surfaces. In the embodiment not shown, each of the first limitation surface 176 and the second limitation surface 177 may also be configured as a combination of a plurality of straight surfaces and curved surfaces, as long as the variable slope design is satisfied.

To further improve the clamping effect and application range of the clamping jaws 160, the slope of the first limitation surface 176 and/or the slope of the second limitation surface 177 at the first end 174 may be designed as small as possible. In other words, an included angle between the first limitation surface 176 and/or the second limitation surface 177 at the first end 174 and a central plane P vertically bisecting the second guide member 151 is as small as possible.

As an implementation, the slope of the line formed by the intersection of the first limitation surface 176 and/or the second limitation surface 177 and the horizontal plane relative to the longitudinal straight line on the horizontal plane at the first end 174 is less than or equal to 0.3. Optionally, the slope of the line formed by the intersection of the first limitation surface 176 and/or the second limitation surface 177 and the horizontal plane relative to the longitudinal straight line on the horizontal plane at the first end 174 is less than or equal to 0.1. Optionally, the slope of the line formed by the intersection of the first limitation surface 176 and/or the second limitation surface 177 and the horizontal plane relative to the longitudinal straight line on the horizontal plane at the first end 174 is less than or equal to 0.05. It is easy to understand that the slope of the line formed by the intersection of the first limitation surface 176 and/or the second limitation surface 177 and the horizontal plane relative to the longitudinal straight line on the horizontal plane at the first end 174 is as close as possible to 0.

In other words, the included angle between the first limitation surface 176 and/or the second limitation surface 177 at the first end 174 and a central plane P vertically bisecting the second guide member 151 is optionally less than 5°, or even less, e.g., approximately equal to 0°.

Thus, a slope of a plane tangent to the first limitation surface 176 and/or the second limitation surface 177 at the first end 174 relative to the second guide member 151 is the smallest, and the biasing mate 163 is wedged against the first limitation surface 176 when it is at the first end 174, so that a direction of the force of the spring to the biasing mate 163 has the smallest component in a direction in which the clamping jaws 160 are open and the largest component in the direction of the second guide member 151, and the clamping jaws 160 can be easily in the clamping state and remain in that state, so that the clamping jaws 160 are less likely to open in an unexpected situation.

Referring to FIG. 1, FIG. 2, FIG. 3, FIG. 4, and FIG. 6, the handle 180 is pivotally disposed on the adapter body 140 and is mounted at an upper panel 141. Specifically, the handle 180 includes a hinge part 183, an operating part 181, and an execution part 182. The operating part 181 is at the top of the handle 180, and is configured to operate by an operator. The execution part 182 is at the bottom of the handle 180 and is movably connected to the movable member 170. The hinge part 183 is disposed between the operating part 181 and the execution part 182, the handle 180 is connected to the adapter body 140 via the hinge part 183. The upper panel 141 defines an opening, and at least part of the handle 180 extends into the adapter body 140 through the opening, so that at least part of the execution part 182 is disposed in the adapter body 140, and at least part of the operating part 181 is disposed outside the adapter body 140.

Specifically, the operating part 181 is disposed outside the adapter body, the execution part 182 is disposed in the adapter body, and the operating part 181 and the execution part 182 each are connected to the hinge part 183. The operating part 181 includes a first arm portion 184 integrally connected with the hinge part 183, and the execution part 182 includes a second arm portion 185 integrally connected with the hinge part 183. In other words, the operating part 181 is connected to the hinge part 183 via the first arm portion 184, and the execution part 182 is connected to the hinge part 183 via the second arm portion 185. An operating portion of the operating part 181 is disposed at an end of the first arm portion 184, and an execution portion of the execution part 182 is disposed at an end of the second arm portion 185. The first arm portion 184 and the second arm portion 185 each have a relatively flat structure. The operating part 181, the hinge part 183, and the execution part 182 may be integrally formed, or may be formed by a plurality of fittings in a fixed assembly.

In this embodiment, the movable member 170 defines a matching groove 172, the execution part 182 is configured as a sliding member that is slidably disposed in the matching groove 172, i.e., the matching groove 172 may be configured as a sliding groove. In the embodiment not shown, the execution part 182 may also be configured as a rolling member to reduce the friction, such as a roller or a bearing. In this case, the execution part 182 is rollable within the matching groove 172.

When the operator operates the operating part 181, or when the operator pulls the handle 180, the handle 180 is pivotable with the hinge part 183 as the axis. Accordingly, the execution part 182 of the handle 180 is configured to pull the movable member 170 to move along the guiding direction of the second guide member 151. Specifically, the operating part 181 of the handle 180 is movable in a first circular arc with the hinge part 183 as an axis and the distance between the operating part 181 and the hinge part 183 as a radius. The execution part 182 of the handle 180 is movable in a second circular arc with the hinge part 183 as an axis and the distance between the execution part 182 and the hinge part 183 as a radius. The movable member 170 moves in a straight line with the interference of the execution part 182 for a distance that is a component of the second circular arc in a horizontal direction.

Thus, the handle 180 can pull the movable member 170 via the execution part 182 to move along the guiding direction of the second guide member 151, thereby changing positions of the clamping jaws 160 through the interaction between the biasing part 171 and the biasing mate 163, i.e., changing the distance between a pair of clamping jaws 160.

When the clamping jaws 160 are in the clamping state, the handle 180 is in an initial position, i.e., the execution part 182 and the operating part 181 are in the initial position. When the clamping jaws 160 are in the open state, the handle 180 is in a working position, i.e., the execution part 182 and the operating part 181 are in the working position. In an embodiment, the first arm portion 184 is in a state close to being erect when the operating part 181 is in the initial position, and the first arm portion 184 is lying horizontally or flatly, or in a state close to lying horizontally or flatly when the operating part 181 is in the working position. Similarly, the second arm portion 185 is in a state close to being erect when the execution part 182 is in the initial position, and the second arm portion 185 is in a state close to lying horizontally or flatly when the execution part 182 is in the working position. That is, in the initial position, the movable member 170 is moved away from the cannula 110 by the elastic force, and the handle 180 is erected under the action of the movable member 170. When the clamping jaw 160 and the cannula 110 have the largest distance, the handle 180 is in a flat state, which may be represented as a horizontal lying state or a flat lying state. At this time, the operator pulls the handle 180 so that the movable member 170 approaches the cannula 110 with the interference of the execution part 182 and tends to be horizontal. In other words, when the handle 180 is close to a horizontal state, i.e., close to a locked state, the operator does not need to press the handle with great force to maintain the clamping jaws 160 in the open state.

Optionally, the upper surface of the adapter body 140 is further provided with an avoidance part (not shown), and the operating part 181 and the first arm portion 184 may be inserted into the avoidance part when the operating part 181 is in the working position.

The above design of the handle 180 ensures that the operator can press the operating part 181 with a small operating force to cause the clamping jaws 160 to open to a limit position, so that the operator can concentrate on the engagement of the cannula 110 and the cannula adapter 130 without being distracted by the force to maintain the handle 180.

In order to avoid obstacles to facilitate smooth rotation of the handle 180, the operating part 181 and the execution portion 182 are at least partially odd-symmetric or quasi-odd-symmetric with respect to the hinge part 183. That is, the operating part 181, the execution part 182, and the hinge part 183 are not on the same straight line, or are not coplanar. On the contrary, as shown in the figures, the operating part 181 is disposed on one side of the hinge part 183, and the execution part 182 is disposed on the other side of the hinge part 183. In other words, an extension direction of the operating part 181 and an extension direction of the execution portion 182, i.e., the first arm portion 184 and the second arm portion 185, are both optionally tangent to the hinge part 183.

In addition, the initial position and the working position of the execution part 182 are both located on the same side of the hinge part 183. In other words, a position of the execution part 182 changes very little from the initial position to the working position. That is, moment arms of the execution part 182 in the initial position and the working position form an acute angle, which means that a moving length of the execution part 182 is small, allowing the operator to save more effort.

In some embodiments, the operating part 181 and the execution part 182 may also be central symmetry in other forms. For example, an angle between the first arm portion 184 and the second arm portion 185 is less than 180°, the first arm portion 184 or the operating part 181 is in an erected state in the initial position and in another erected state in the working position, and a state of the second arm portion 185 or the execution part 182 follows a change from erect to lying.

Unless otherwise defined, the technical and scientific terms used herein have the same meaning as commonly understood by one of ordinary skill in the technical field of the present disclosure. The terminology used herein is for the purpose of describing particular embodiments only and is not intended to be limiting of the present disclosure. The features described herein in one embodiment may be applied to another embodiment separately or in combination with other features unless the features are not applicable or otherwise described in this other embodiment.

The present disclosure has been described in the above embodiments, but it should be understood that the above embodiments are for the purpose of illustration and description only and are not intended to limit the present disclosure to the scope of the described embodiments. In addition, those skilled in the art may understand that the present disclosure is not limited to the above embodiments, and more variations and modifications may be made according to the teachings of the present disclosure, and these variations and modifications fall within the protection scope of the present disclosure. The protection scope of the present disclosure is defined by the appended claims and their equivalents.

The invention claimed is:

1. A cannula adapter configured to hold a cannula of a surgical robot, comprising:

- an adapter body;
- a first guide rail extending along a first direction and fixedly disposed in the adapter body;
- at least one clamping jaw disposed in the adapter body and movably coupled to the first guide rail, wherein the at least one clamping jaw is translationally movable along the first guide rail between a first position and a second position without rotating relative to the adapter body;
- an operating actuation mechanism; and
- a follower mechanism including a movable member movably coupled to the adapter body and configured to be driven by the operating actuation mechanism to translationally move in a second direction transverse to the first direction without rotating relative to the adapter body;
- wherein the at least one clamping jaw is movably coupled to the movable member, such that translational movement of the movable member relative to the adapter body in the second direction drives the at least one clamping jaw to translationally move along the first guide rail, the at least one clamping jaw is in the first position when the movable member is in a third position, and the at least one clamping jaw is in the second position when the movable member is in a fourth position.

2. The cannula adapter according to claim 1, wherein an included angle between the first direction and the second direction is in a range of 85° to 90°.

3. The cannula adapter according to claim 1, wherein the at least one clamping jaw includes two clamping jaws, the two clamping jaws are configured to be driven concurrently by the operating actuation mechanism to translationally move in two opposite directions, respectively.

4. The cannula adapter according to claim 1, wherein two clamping jaws are provided, the two clamping jaws are configured to be driven concurrently by the operating actuation mechanism to translationally move, and an included angle between directions in which the two clamping jaws are translationally moved is in a range of 170° to 180°.

5. The cannula adapter according to claim 1, wherein the movable member includes a track surface, and one of a roller and a bearing is connected between the at least one clamping jaw and the track surface and is movable along the track surface; and wherein the track surface has both a component in the first direction and a component in the second direction.

6. The cannula adapter according to claim 5, wherein the first direction is perpendicular to the second direction.

7. The cannula adapter according to claim 1, further comprising an elastic assembly connected to the follower mechanism and configured to bias to the movable member to the third position, so as to bias the at least one clamping jaw to the first direction, and on the condition that the at least one claiming jaw to the first direction, the at least one clamping jaw is configured to apply a clamping force to the cannula.

8. The cannula adapter according to claim 1, further comprising a second guide rail, wherein the second guide member is fixedly disposed with respect to the adapter body, the second guide rail supports the movable member, and the movable member is movably coupled to the second guide rail.

9. A surgical robot, comprising a cannula adapter, wherein the cannula adapter is configured to hold a cannula of the surgical robot, and includes:

- an adapter body;
- a first guide rail extending along a first direction and fixedly disposed in the adapter body;
- at least one clamping jaw disposed in the adapter body and movably coupled to the first guide rail, wherein the at least one clamping jaw is translationally movable along the first guide rail between a first position and a second position without rotating relative to the adapter body;

an operating actuation mechanism; and a follower mechanism including a movable member movably coupled to the adapter body and configured to be driven by the operating actuation mechanism to translationally move in a second direction transverse to the first direction without rotating relative to the adapter body;

wherein the at least one clamping jaw is movably coupled to the movable member, such that translational movement of the movable member relative to the adapter body in the second direction drives the at least one clamping jaw to translationally move along the first guide rail, the at least one clamping jaw is in the first position when the movable member is in a third position, and the at least one clamping jaw is in the second position when the movable member is in a fourth position.

10. The cannula adapter according to claim 7, further comprising a handle hinged to the adapter body and movably coupled to the movable member, wherein the movable member translationally moves in the second direction to the fourth position when the handle is actuated to rotate relative to the adapter body.

11. The cannula adapter according to claim 10, wherein the movable member defines a groove, the handle has a rolling member movably received within the groove, the rolling member is movable in a third direction relative to the movable member, and the third direction is perpendicular to both the first direction and the second direction.

12. The cannula adapter according to claim 1, wherein the movable member defines at least one slot, and each of the at least clamping jaw has a roller movably received in a respective one of the at least one slot, the roller is movable relative to the movable member following a track on a plane defined by the direction and the second direction and transvers to both the first direction and the second direction.

13. The cannula adapter according to claim 12, wherein the track is straight or curved.

14. The cannula adapter according to claim 12, wherein two clamping jaws are provided, and the movable member defines two slots, the two slots are symmetrically arranged about a plane perpendicular to the first direction.

15. The cannula adapter according to claim 12, wherein the movable member has two surfaces defining one of the at least on slot, the two surfaces are opposite each other and extend parallelly, a slope of a plane tangent to one of the two surfaces about the second direction varies gradually in the first direction.

16. The cannula adapter according to claim 1, wherein the movable member has at least one first limitation surface, each of the at least clamping jaw has a roller configured to roll on a respective one of the at least one first limitation surface when the movable member is moved from the third position to the fourth position, such that the at least one jaw is moved from the first position to the second position.

17. The cannula adapter according to claim 16, wherein the at least one first limitation surface is perpendicular to a plane defined by the direction and the second direction, and an intersection between the at least one first limitation surface and the plane is a line or a curve transvers to both the first direction and the second direction.

18. The cannula adapter according to claim 16, wherein the movable member has at least one second limitation surface, each roller of the at least clamping jaw is configured to roll on a respective one of the at least one second limitation surface when the movable member is moved from the fourth position to the third position, such that the at least one jaw is moved from the second position to the first position.

19. The cannula adapter according to claim 18, wherein the at least one second limitation surface is perpendicular to a plane defined by the direction and the second direction, and an intersection between the at least one first limitation surface and the plane is a line or a curve transvers to both the first direction and the second direction.

20. A cannula adapter for a surgical robot, comprising:

an adapter body;

a first guide rail extending along a first direction and fixedly disposed in the adapter body;

at least one clamping jaw disposed in the adapter body and movably coupled to the first guide rail, wherein the at least one clamping jaw translationally movable along the first guide rail;

an operating actuation mechanism; and a follower mechanism including a movable member movably coupled to the adapter body and configured to be driven by the operating actuation mechanism to translationally move in a second direction transverse to the first direction;

wherein the movable member defines at least one slot, and each of the at least one clamping jaw has a roller movably received in a respective one of the at least one slot, the roller is movable relative to the movable member along a track on a plane defined by the first direction and the second direction, such that the at least one clamping jaw is moved along the first guide rail when the movable member is moved in the second direction.

* * * * *